United States Patent [19]
Bullock et al.

[11] Patent Number: 4,796,615
[45] Date of Patent: Jan. 10, 1989

[54] CONNECTOR FOR ESOPHAGEAL PROBE

[75] Inventors: James K. Bullock, Burbank; L. Arnold Mann, Valencia; Daniel R. Kuni, Saugus, all of Calif.

[73] Assignee: Baxter Travenol Laboratories, Inc., Deerfield, Ill.

[21] Appl. No.: 920,290

[22] Filed: Oct. 16, 1986

[51] Int. Cl.⁴ .............................................. A62B 9/04
[52] U.S. Cl. .............................. 128/202.27; 604/283
[58] Field of Search ................................. 128/4–8, 128/202.27, 203.13; 403/349; 604/264, 280, 283, 284

[56] References Cited

U.S. PATENT DOCUMENTS

| | | | |
|---|---|---|---|
| 1,171,380 | 2/1916 | Arthur | 403/349 |
| 3,805,794 | 4/1974 | Schlesinger | 604/283 |
| 3,858,910 | 1/1975 | Oetiker | 403/349 |
| 4,502,490 | 3/1985 | Evans et al. | |
| 4,551,146 | 11/1985 | Rogers | 604/283 |
| 4,601,701 | 7/1986 | Mueller | 604/280 |

FOREIGN PATENT DOCUMENTS

| | | | |
|---|---|---|---|
| 0151519 | 8/1985 | European Pat. Off. | 604/283 |
| 8502101 | 5/1985 | PCT Int'l Appl. | 128/4 |

Primary Examiner—Max Hindenburg
Attorney, Agent, or Firm—Paul C. Flattery; Martey R. Perman; Clarence A. Green

[57] ABSTRACT

A quick disconnect connector for use with a system for measuring depth of anaesthesia of a patient. For this purpose, a probe is attached to a patient to detect esophageal contractions. The probe is connected to a patient station by means of flexible tri-lumen tubing. The patient station provides a pressure transducer, a source of pressurized air, and a thermistor connection, and in turn is operatively connected to a microprocessor which controls the entire operation. One conduit of the tubing enables communication between a liquid filled balloon within the probe and the transducer at the patient station. Another conduit enables an air balloon within the probe to be connected to the source of pressurized air. Still another conduit receives the electrical lead which extends to the thermistor. The connector is designed to be joined with the tri-lumen tubing at one end, and at its other end is provided with a positive locking construction enabling the probe to be rapidly connected to the source of pressurized air or rapidly disconnected therefrom. For this purpose, the patient station has a female receptacle which matingly receives a male bayonet style fitting on the connector and a resilient gasket on the receptacle is engaged by a terminal rim on the connector to thereby achieve a fluid tight junction.

11 Claims, 3 Drawing Sheets

CONNECTOR FOR ESOPHAGEAL PROBE

BACKGROUND OF THE INVENTION

I. Field of the Invention

The present invention relates generally to patient monitoring equipment in the form of a probe attached to the patient for measuring anaesthesia based on esophageal contractions and, specifically, to a quick disconnect connector which joins the probe with the remainder of the system located distant from the patient.

II. Description of the Prior Art

The present invention has application in monitoring the depth of anaesthesia of patients to whom anaesthetic or sedative drugs are administered. The term anaesthesia is used herein in its broadest sense and is intended to include not only anaesthesia for surgery, but also the lighter levels of anaesthesia or sedation used in critically ill patients receiving intensive care. The term anaesthetic is to be understood accordingly.

The response of individual patients to drugs is highly variable. Especially in the case of anaesthetic drugs, an anaesthetist is required to employ a considerable degree of clinical judgment in order to obtain an optimum effect. Clinical anaesthesia is not an "on-off" state but a state of unconsciousness and variable reflex suppression produced by one or more drugs. It is traditional to describe the degree of reflex suppression as the depth of anaesthesia. At present, the depth of anaesthesia is judged by the change in various clinical signs produced in response to surgical stimulus. It has been recognized to be of great assistance if some objective information were available indicating the depth of anaesthesia. Attempts have been made to use indirect measurements of a patient's vital physiological functions such as heart rate, blood pressure and electroencephalogram (EEG) waveforms to indicate depth of anaesthesia. However, none of these measurements alone has proved to be a sufficiently reliable index of depth of anaesthesia.

An article by P. Suppan in the British Journal of Anaesthesia, (1972) 44, p. 1263 describes the use of pulse rate as an indicator of depth of anaesthesia, and describes furthermore the use of a feed-back system to automatically control anaesthetic administration. The article also describes the possibility of using blood pressure as an indicator of the depth of anaesthesia, but there is no suggestion of the combined use of the parameters, or any suggestion that combining two or more measurements to produce a 'score' can provide a more reliable indication of depth of anaesthesia.

M. Dubuis, D. E. Scott, and T. M. Savege, in an article in Annals Anaesthesia, France (1979) 3, p. 215, describe the use of EEG as an indicator of the after effects of anaesthesia.

Electronically processed EEG signals have been employed to monitor the level of electrical activity in the brain during anaesthesia. A review of this and other applications of EEG monitoring is given in Monitoring Cerebral Function (author P. F. Prior, published by Elsevoir (North-Holland Biomedical Press, 1979, Amsterdam).

Finally, J. S. Stewart in The Lancet (1969) 1, p. 1305 describes a monitoring system for drawing the attention of a clinician to a deteriorating condition of a patient, using a combination of various parameters, such as heart rate, blood pressure, and oxygen tension. There is, however, no suggestion in the Stewart article of the use of a similar system to measure depth of anaesthesia.

The patentees, John M. Evans and Colin C. Wise, of U.S. Pat. No. 4,502,490 issued Mar. 5, 1985 entitled "Patient Monitoring Equipment, Probe for Use Therewith, and Method of Measuring Anaesthesia Based on Oesophagal Contractions" have discovered that the muscular activity in the esophagus is related to the depth of anaesthesia. The disclosure of the aforesaid U.S. Pat. No. 4,502,490 is incorporated herein in its entirety and made a part hereof.

During light anaesthesia there is a great deal of smooth muscle activity in the form of periodic contractions. During deep anaesthesia there is little esophageal smooth muscle activity. Evans and Wise consistently observed this relationship between esophageal activity and depth of anaesthesia with most common anaesthetic agents. Changes in esophageal muscle activity cause corresponding changes in intralumenal esophageal pressure. Thus, by insertion of a balloon-type catheter, or some other suitable pressure probe, into the esophagus, and measuring the internal pressure in the esophagus, they found it is possible to obtain an indication of the depth of anaesthesia.

The pressure changes produced by esophageal contraction generally last 2-4 seconds and occur at frequencies of up to 4 or 5 per minute during light anaesthesia. Occasionally there are short periods of rapid contractions at rates of up to 15 per minute accompanied by high resting pressures between contractions.

Evans and Wise also discovered that, whether or not esophageal contractions are used as a measure of the degree of anaesthesia, increased reliability in the quantification by the anaesthetist of depth of anaesthesia can be obtained if a plurality of different bodily functions are observed, and a score value assigned to each in accordance with certain parameters.

The score values may then be summed to produce a total score indicative of the degree of anaesthesia of the patient.

As disclosed in the aforementioned U.S. Pat. No. 4,502,490, a convenient means of provoking the esophageal contractions is an air or liquid filled inflatable balloon inserted into the trachea or, more preferably, the esophagus. As explained in the patent, such a probe inserted into the esophagus can include a liquid filled monitor balloon and an air filled provoking balloon which is caused to expand and contract on a periodic basis. There are times which occur in the course of surgery when it is desired to rapidly either connect the air or gas filled balloon to the pressurized source or to disconnect it therefrom. It is desired that such a connection and disconnection be achieved in an easy and rapid action requiring only one hand for the procedure. In the past, connectors have been utilized which attached at one end to flexible plastic tubing which extended from the probe, the other end being tapered and intended for a press fit engagement with a metallic fitting adjacent the source of pressurized air or gas.

This arrangement often times required two hands to achieve, did not assure a uniformly tight connection each time, and was not of a positive nature such that it could become loosened with vibration and work itself free if left unattended.

SUMMARY OF THE INVENTION

It was with knowledge of the prior art and the problems existing which gave rise to the present invention.

According to the invention, a quick disconnect connector is provided for use with a system for measuring depth of anaesthesia of a patient.

For this purpose, a probe is attached to a patient to detect esophageal contractions. The probe is connected to a patient station by means of flexible tri-lumen tubing. The patient station provides a pressure transducer, a source of pressurized air, and a thermistor connection, and in turn is operatively connected to a microprocessor which controls the entire operation. One conduit or passageway of the tubing enables communication between a light filled balloon within the probe and the transducer at the patient station. Another passageway enables a provoking air balloon on the probe to be connected to the source of pressurized air. Still another passageway receives the electrical lead which extends to the thermistor. The connector is designed to be joined with the trilumen tubing at one end, and at its other end is provided with a positive locking construction enabling the probe to be rapidly connected to the source of pressurized air or rapidly disconnected therefrom. For this purpose, the patient station has a female receptacle which matingly receives a male bayonet style fitting on the connector and a resilient gasket on the receptacle is engaged by a terminal rim on the connector to thereby achieve a fluid tight junction.

The connector of the invention is particularly adapted to use with the tri-lumen tubing. Although known connectors have been used with tri-lumen tubing, it has been customary for a connector to be attached to the tubing in such a manner that it serves to enable communication through the connector of only one passageway of the tubing. For this reason, it has been customary to provide suitable exits through the outer wall of the tubing for the remaining passageways of the tubing and these exits are positioned in the tubing at a location prior to reaching the end to which the connector is attached.

In contrast, the connector of the invention serves to accommodate the construction of the tri-lumen tubing and enables communication therethrough of at least two of the passageways of the tubing or, alternatively, all three of the passageways.

Furthermore, the connector of the invention is readily attached to the tri-lumen tubing and, in a one handed operation, can be readily attached to or detached from the receptacle to a source of pressurized air or gas. When the connector is attached to the receptacle, it provides a fluid tight connection as well as a positive connection which can not become inadvertently loosened by the vibration or otherwise.

It will be appreciated that although the disclosure is particularly directed to use of the connector with trilumen tubing, the invention is not to be so limited. That is, the connector may be used with single lumen tubing or with multi-lumen tubing with equal success.

Other and further features, objects, advantages, and benefits of the invention will become apparent from the following description taken in conjunction with the following drawings. It is to be understood that both the foregoing general description and the following detailed description are exemplary and explanatory but not restrictive of the invention. The accompanying drawings which are incorporated in, and constitute a part of this invention, illustrate some of the embodiments of the invention and, together with the description, serve to explain the principles of the invention in general terms. Like numerals refer to like parts throughout the description.

DETAILED DESCRIPTION OF THE DRAWINGS

DETAILED DESCRIPTION OF THE PREFERRED EMBODIMENT

Figure 1:
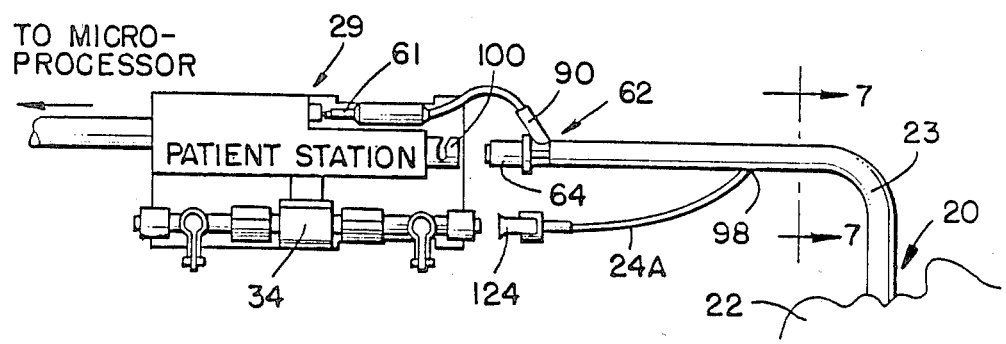
FIG. 1 is a diagrammatic view of a system for monitoring the depth of anaesthesia of a patient to whom anesthetic or sedative drugs have been administered.
Figure 2:
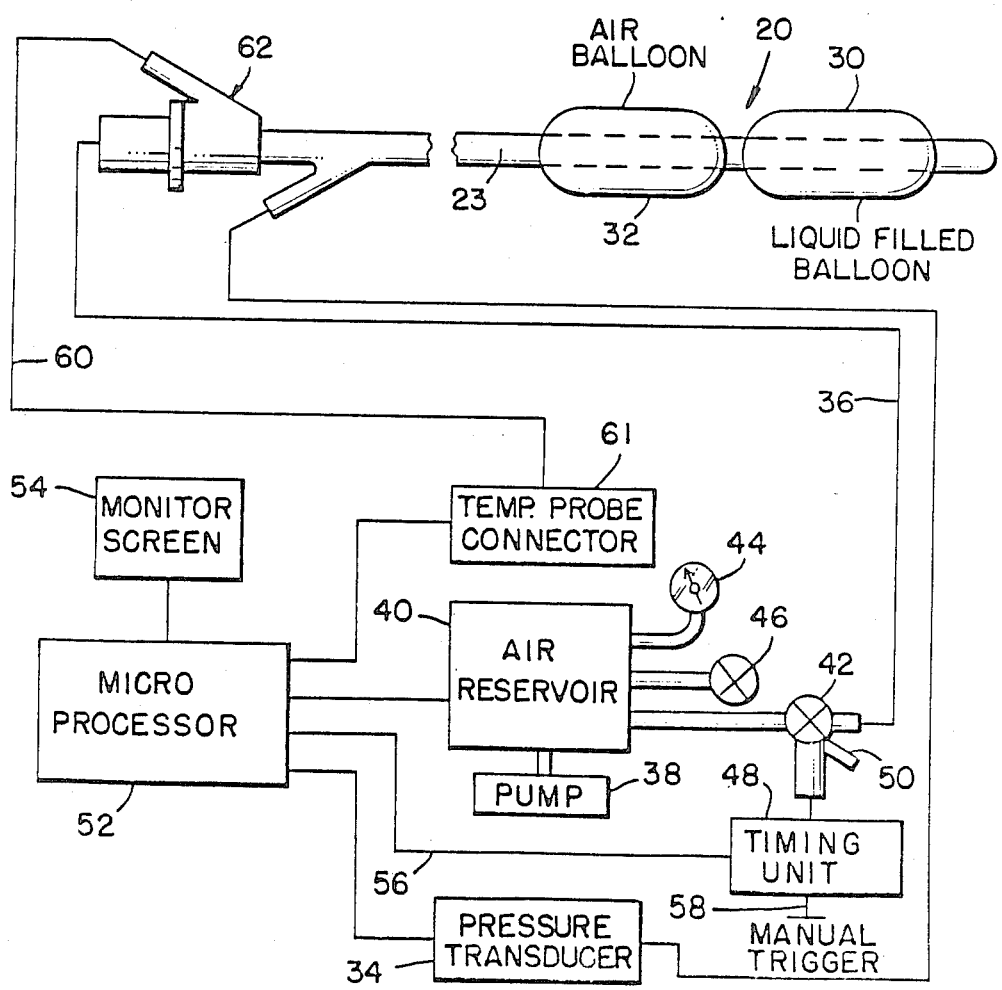
FIG. 2 is a schematic representation of the control system associated with the monitoring system illustrated in FIG. 1.
Figure 3:
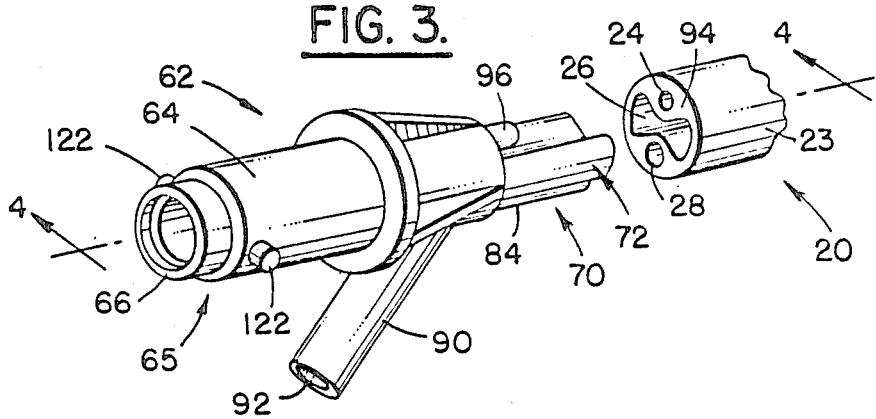
FIG. 3 is a detail exploded perspective view illustrating a quick disconnect connector embodying the invention and a length of tri-lumen tubing with which it is associated.
Figure 4:
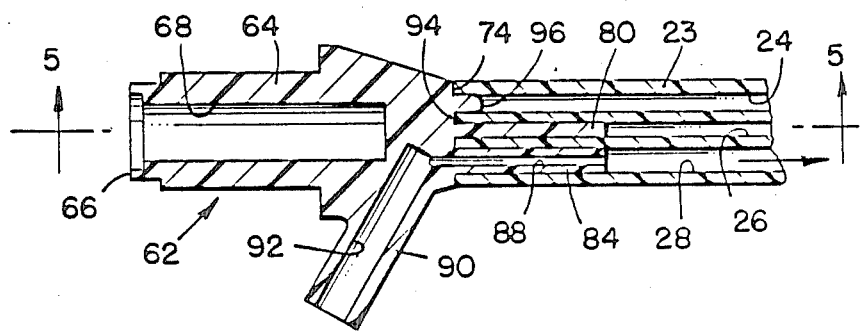
FIG. 4 is a cross section view taken generally along line 4—4 in FIG. 3.
Figure 7:
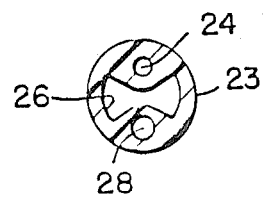
FIG. 7 is a cross section view of the tri-lumen tubing taken generally along line 7—7 in FIG. 1.

Referring initially to FIGS. 1 and 2, there is shown therein a probe 20 which is adapted to be inserted into the esophagus of a patient 22. The probe 20 comprises hollow flexible tubing 23 of PVC or other suitable plastic material and, preferably, of tri-lumen construction, which contains three conduits or passageways 24, 26 and 28 (FIGS. 3, 4 and 7). The tubing 23 extends between a proximal end at the patient and a distal end at a patient station 29. At the proximal end of the probe there is provided a balloon 30 which is connected to passageway 24 and adjacent to balloon 30 is a further balloon 32 coupled to passageway 26. The balloon 30 is liquid-filled and passageway 24 is coupled to a pressure transducer 34 so that the external pressure applied to the balloon can be monitored. A suitable length of the tubing 23 is about 100 cm while the total length of the two balloons 30 and 32 can be about 10 cm. The two balloons each have a maximum diameter of approximately 2 cm when inflated to a pressure of approximately eight psig.

Passageway 26 is connected to an air or gas supply line 36. Throughout the specification, the term air will be used to refer to either air or any other suitable gas. An air pump 38 supplies a reservoir 40 which feeds the supply line 36 through a valve 42. A pressure gauge 44 is coupled to the reservoir 40. In an alternative and preferred embodiment, the gauge 42 may be coupled to the line 36 so as to measure the provoking pressure directly. Reservoir 40 also has a regulating valve 46 which can be adjusted to prevent an excessive pressure rise in the reservoir. Valve 40 is controlled by a suitable timing unit 48.

In the use of the equipment shown in FIG. 1, probe 20 is inserted into the esophagus so that the balloon 30 is in the lower part of the esophagus. In an adult, this is typically 35 cm from the incisor teeth. The timing unit 48 operates the control valve 42 to connect reservoir 40 to intermittently inflate balloon 32. At the end of each inflation period, the valve 42 connects line 36 to a vent 50 to allow the balloon to deflate. With the reservoir 40 typically having a volume of approximately 200 cc and being held at a pressure of around 200 mm Hg and with balloon 32 having an inflated volume of about 5 cc, the opening of valve 40 will cause full and rapid expansion of balloon 32 to its maximum capacity. It is convenient to hold balloon 32 inflated for periods of 5 seconds or thereabouts with the intervals between inflations being in the range of 1–10 mins.

In order to safeguard against deleterious effects on a patient rising out of rupture of the balloon 32, it may be desirable to provide means for limiting the volume or rate of airflow out of the reservoir 40. A second valve (not shown) may be provided, operated by the timing unit 48, between the air pump 38 and the reservoir 40 and open when valve 42 is closed, to restore pressure in the reservoir 40 only when the reservoir is not directly connected to balloon 32.

Any contraction of the esophagus which is either spontaneous or else is triggered by inflation of balloon 32 is monitored by the liquid-filled balloon 30 and a pressure signal therefrom is fed through passageway 24 to pressure transducer 34. The pressure signal obtained from the balloon 30 provides an output signal of magnitude proportional to the amplitude of the pressure signal fed to it. The transducer 34 may include offset and gain controls.

The monitor balloon 30 described above is liquid filled, preferably with water. It is, however, possible to use an air or gas filled balloon for monitoring purposes although in such cases there may be a loss of fidelity in the recording of pressure amplitude. Alternatively, in place of a balloon, a catheter tip transducer can be inserted into the esphagus in a soft balloon sleeve, in the position of balloon 30.

While a separate monitoring balloon 30 and provoking balloon 32 have been described with reference to FIGS. 1 and 2, it is possible to replace the two balloons by a single balloon which fulfills both functions. In such a case, a switching valve is required which normally connects the balloon 30 to the pressure transducer 34 but which is switched to valve 42 whenever a provoking stimulus is called for by the timing unit 48.

Control of the system illustrated in FIG. 2 may be performed by an appropriately programmed microprocessor 52 and desired bodily functions displayed on a suitable screen 54. The microprocessor 52 is illustrated in greater detail in FIG. 2 of the aforesaid U.S. Pat. No. 4,502,490.

The timing unit 48 may be optionally provided with an inhibit input along a line 56 as directed by the mircoprocessor 52. When an inhibit pulse is received, the timing unit 48 does not function for a set period of time thereafter so that inflation of the provoking balloon 32 is inhibited during that period. The inhibit pulses are derived from the pressure transducer 34 to which balloon 30 is coupled. Use of the inhibit pulses ensures that when there are spontaneous contractions, operation of the provoking balloon 32, which is then unnecessary, is prevented. A further option provides for manual triggering (diagrammatically represented by a button 58) of the timing unit 48 to operate the valve 42.

The output signal from the transducer 34 includes not only major signals derived from esophageal contractions but also other signals which arise from heartbeats and lung ventilation as well as other background signals including noise. The output signal from the transducer 34 is applied to a filter to remove low level background signals and thence to an adjustable threshold circuit to block all remaining signals below a set level. Since the esophageal contractions result in pressure signals of a much higher level of amplitude than signals from other sources, the setting of an appropriate threshold level in the circuitry ensures that the output therefrom comprises signals due solely to the esophageal contractions.

The filtered pressure signals are utilized to provide a count of events in a moving time "window". The count is made in a suitable timer/counter circuit within the microprocessor 52 into which the desired duration of the time "window" is entered. Conveniently, the circuit has a plurality of registers, each of which records the inputs received that exceed the threshold value during a fixed time period (e.g. one minute) in succession. The number of the most recently filled registers that contribute their contents to the summation is determined by the length of the time "window". Thus for one minute registers and a time "window" of four minutes, the four last-filled registers are summed and their sum is outputted. The above example of a one minute time period and a time window of four minutes is purely to illustrate the manner of operation of the circuitry and a different time period can be provided in the circuit and length of the time "window" may be adjustable for greater or smaller durations than the figure quoted. The summation of the register contents may be adjusted to bias the sum in favor of some part of the "window".

The input to the microprocessor include the signal from the aforementioned filter as well as the various set values such as pressure threshold, window length and other desired information concerning contractions. The output from the microprocessor 52 may include display information, as on a screen 54.

Before being processed, signals from the transducer 34 may be converted from analog to digital form, and the digitized form of the input may be connected directly to the microprocessor circuitry. Using this technique it is possible for the microprocessor to compare the output signal directly with a pre-programmed "norm", as regards, for example, amplitude, duration, and profile or "shape". If the signal fits the pre-set norm the waveform is recognized as a significant contraction. Clearly it may be useful to employ a threshold discriminator in combination with the above technique.

The esophageal probe 20 may have incorporated therein a microphone, a temperature probe, or electrodes for recording an electrocardiogram. The microphone may be either incorporated in the region of the probe tip, or else connected either to the provoking passageway 26 or sensing passageway 36, sound from the esophagus being transmitted by the intermediate fluid. Thus, an amplified stethoscope function may be provided. Similarly, a thermistor 60 may be provided to record body temperature, the thermistor extending to an associated temperature probe connector 61 located at the patient station 29.

It was previously mentioned that in the course of a surgical procedure, it may be desirable, and even necessary, to rapidly either connect the probe 20 to the patient station 29 or to disconnect it therefrom. To this end, a unique quick disconnect connector 62 has been devised as particularly well seen in FIGS. 3-5. In a manner which will be fully explained momentarily, the connector 62 is readily insertable into an end of the tubing 23 and, at its opposite end, can be quickly attached to the patient station while assuring a fluid tight junction. The connector 62, which may be formed of any suitable plastic material such as rigid PVC has a main body 64 which is generally of a cylindrical configuration. A first end 65 of the connector 62 terminates at a rim 66 which defines an opening into a chamber 68 encompassed within the main body.

Figure 5:
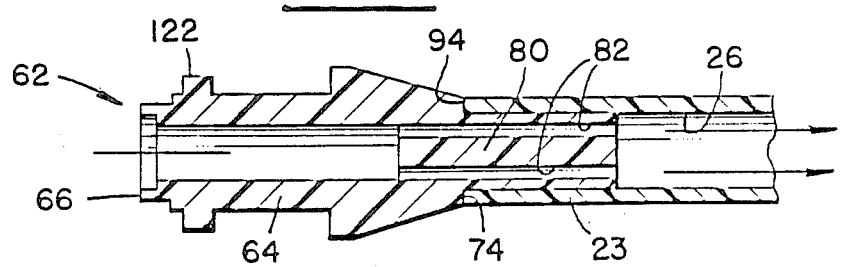
FIG. 5 is a cross section view taken generally along line 5—5 in FIG. 4.
Figure 6:
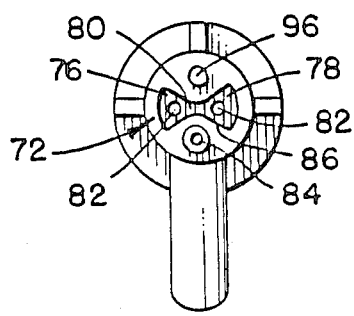
FIG. 6 is an end elevational view of one end of the connector.

The connector 62 also includes a second end 70 opposite the first end 65. A centrally disposed elongated member 72, generally aligned with the longitudinal axis of the main body 64, is integral with the main body and extends in a direction away from a transverse terminal surface 74 thereof (FIGS. 4 and 5). As seen particularly well in FIG. 6, the elongated member 72 has a shape, in cross section, resembling a bow tie although the shape may be altered to accommodate any multi-lumen tubing configuration. In this regard, it includes an integral pair of enlarged sections 76, 78 in side by side relationship joined by a central web member 80, the enlarged sections 76, 78 and the central web member 80 all extending for the entire length of the elongated member 72. As seen in FIGS. 5 and 6, each of the enlarged sections 76, 78 includes a longitudinally extending passageway 82 which extends therethrough and communicates with the chamber 68. Of course, it will be understood that the dual passageway design as best illustrated in FIG. 6 may be replaced with another construction such as a single passageway, or even multiple passageways.

Viewing FIGS. 3 and 4, a lower elongated member 84, generally parallel with the longitudinal axis of the main body 64, is, like the member 72, integral with the main body and extends in a direction away from the transverse terminal surface 74 thereof. The member 84 has substantially the same length as the member 72 and, as best seen in FIG. 6, is disposed proximate to, or within, a trough defined by a lower surface 86 of the member 72. The lower member 84 also has a passageway 88 (see FIG. 4) extending therethrough.

Connector 62 is also formed with a lower duct member 90 which extends downwardly away from the main body 64 and generally in the direction of the first end 65. A passageway 92 extends the length of the duct member 90 and is so located as to communicate with the passageway 88 in the lower elongated member 84.

As seen in FIGS. 3-5, the second end 70 is adapted to be joined with a terminal end of the tubing 23. In this regard, the elongated member 72 is fittingly received in the passageway 26 and the elongated member 84 is fittingly received in the passageway 28. The tubing 23 is forcibly slipped onto the second end 70 until an extreme end surface 94 of the tubing 23 engages the transverse terminal surface 74 of the connector 62. In this manner, it will be recognized that the passageway 28 thereby comes to be in communication with the passageway 92 and the passageway 26 comes to be in communication with the chamber 68.

With the surfaces 94 and 74 butted together as seen in FIGS. 4 and 5, it is desired to close off the passageway 24 at the connector 62 for a reason which will be described below. For this purpose, a plug member 96 is provided which is integral with the main body 64 and which extends in a direction away from the surface 74.

As best seen in FIG. 4, the plug member 96 is fittingly receivable in a passageway 24 of the tubing 23 to thereby prevent flow of a fluid beyond the connector. The plug member 96 is desired because, in some constructions, as seen for example in FIG. 1, flexible tubing 24A extends from a suitable aperture in the sidewall of the tubing 23 and joins in a fluid tight connection to its associated passageway 24 within the tubing 23. Since this occurs at a location 98 which is indicated as being spaced from the connector 62, there is no reason for flow along that portion of the passageway 24 between the location 98 and the connector 62. The plug member 96 serves to assure that, in any event, there is no flow of fluid beyond the extreme distal end of the tubing 23. To assure that the joint between the second end 70 and the distal end of the tubing 23 is fluid tight, it is desirable to apply some form of bonding agent to the joint. This may be accomplished, for example, by use of a solvent such as that commonly known as "MEK", that is, methyl ethyl ketone. Adhesives may also be used.

Figure 8:
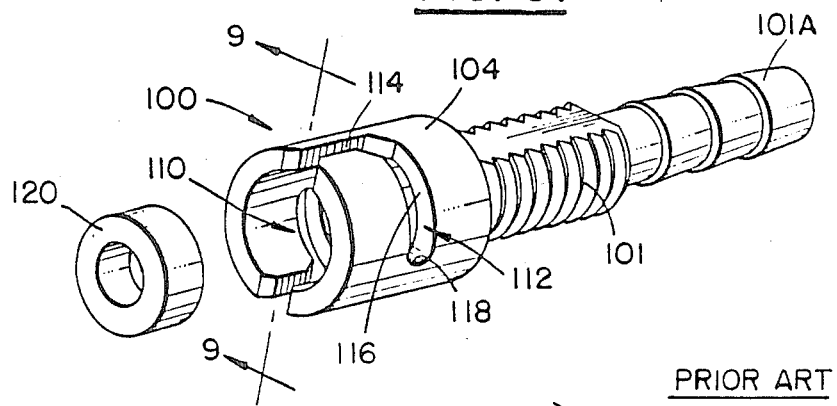
FIG. 8 is a detail perspective view of a female receptacle and an associated gasket exploded therefrom with which the connector of the invention is adapted to be matingly joined.
Figure 9:
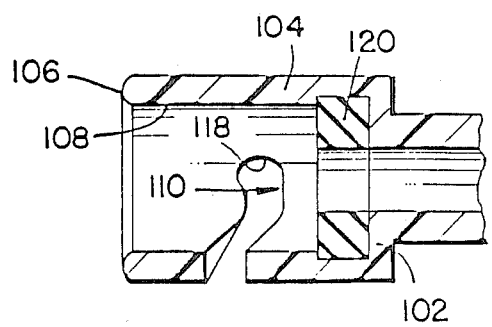
FIG. 9 is a detail cross view section taken generally along line 9—9 in FIG. 8.

With the connector 62 thus joined with the tubing 23, it is desired that the connector be readily attached to the air supply line 36 and, specifically, to a terminal receptacle 100 located at the patient station 29. As particularly well seen in FIGS. 8 and 9, receptacle 100 is of a hollow cylindrical female construction. It has a threaded shank 101 for mounting to the patient station and a nipple 101A for connection with the air supply line 36. The receptacle 100 is formed with a base 102 and a sidewall 104 upstanding from the base terminating at a circular edge 106 which together define a receiving cavity 108.

Formed in the sidewall 104 is a pair of diametrically opposed bayonet slots 110, 112. As indicated with respect to slot 112 in FIG. 8, each slot extends generally parallel to a longitudinal axis for the receptacle 100 for a first distance 114, then curves to extend generally perpendicular to the longitudinal axis for a second distance 116. It will further be appreciated that for the second distance 116, the slots continue to extend in the same parallel, direction, but each continues on to its own terminus 118. The sidewall 104 is preferably recessed adjacent the base 102 (see FIG. 9) to accommodate and retain a gasket 120 of suitable resilient material.

For its part, the connector 62, as seen especially in FIGS. 3 and 5, is constructed such that the first end 65 is cylindrical male element having a pair of radially directed bayonet pins 122 extending in diametrically opposed directions from the main body 64. The first end 65 of the connector 62 is intended to be engaged with the female receptacle 100. To this end, the outer diameter of the main body 64 is slightly less than the inner diameter of the cavity 108, but the pins 122 are of sufficient length to be received in their associated slots 110, 112 and extend at least as far as, or beyond, the outer surface of the sidewall 104.

Thus, with the first end 65 being aligned with the cavity 108, the connector 62 is advanced in the direction of the receptacle 100 such that the pins 122 are received within the first distances 114 of the respective slots 110, 112. The connector 62 is then turned about its longitudinal axis causing the pins 122 to follow into the second distances 116 of their associated slots 110, 112 until each of the pins reaches its associated terminus 118. When that occurs, the rim 66 is firmly engaged with the gasket 120 to thereby achieve a fluid tight connection between the connector 62 and the female receptacle 100 while enabling fluid flow therebetween, that is, between the air reservoir 40 and the probe 20.

In the configuration illustrated in FIGS. 3–5 and with reference to FIG. 1, it can be seen that with the connector 62 joined to the receptacle 100, it is possible to connect the tubing 24A, via a fitting 124, to the pressure transducer 34 at the patient station 29. Similarly, a thermistor lead extending from the probe 20, through the passageways 28, 88, and 92, can then be connected, via a suitable electrical connector 61 to a mating receptacle at the patient station 29 for connection to the thermistor 60. It will also be appreciated that the fitting 124 and connector 61 may remain attached to their mating elements while the connector 62 can be readily detached, if desired. This arrangement is desirable since the thermistor 60 and the transducer 34 are merely passive devices which do not have an effect on the patient. In contrast, the delivery of pressurized air to the balloon 32 has a direct effect on the patient and its use or non-use may be quickly called for, as in an emergency situation.

Figure 10:
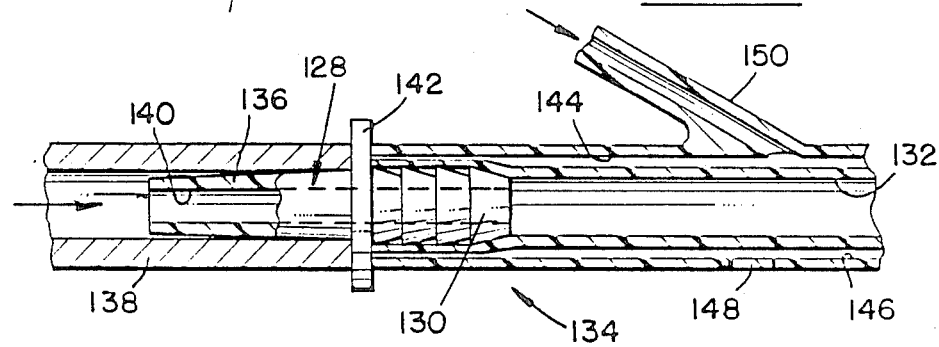
FIG. 10 is a detail side elevation view, in section, illustrating a pair art construction.

The benefits of the connector 62 of the present invention can be more readily appreciated when it is compared to a typical prior art device such as connector 128 illustrated in FIG. 10. Such a connector 128 is typically fabricated from a substantially rigid plastic material, one end 130 being inserted into main passageway 132 of tri-lumen tubing 134, its other end 136 being fittingly received within a typical metallic connector 138. The connector 128 is formed with only one conduit or passageway 140 therethrough, and when the tubing 134 is butted up against a flange 142 of the connector 128, other passageways, 144, 146 are sealed off and do not communicate through the connector itself.

By reason of the construction of the prior art connector 128, since the passageways 144, 146 cannot communicate therethrough, it is necessary to by-pass the connector if those passageways are to be used. Thus, it has been customary to either provide tri-lumen tubing with apertures in its outer wall, or to suitably form them, then to attach in any suitable fashion, other tubing as represented by numerals 148 and 150 to the tubing 134 so that the tubing 148 communicates with the passageway 144 and so that the tubing 150 communicates with the passageway 146. This arrangement, of course, has already been mentioned above and illustrated in FIG. 1 with respect to attachment of tubing 24A to the tubing 23 at the location 98. It will be appreciated that the connector 128 does not provide a positive connection between the tubing 134 and the metallic connector 138 and a tight connection may be difficult to achieve using only one hand. This is in addition to the deficiencies mentioned above.

Figure 11:
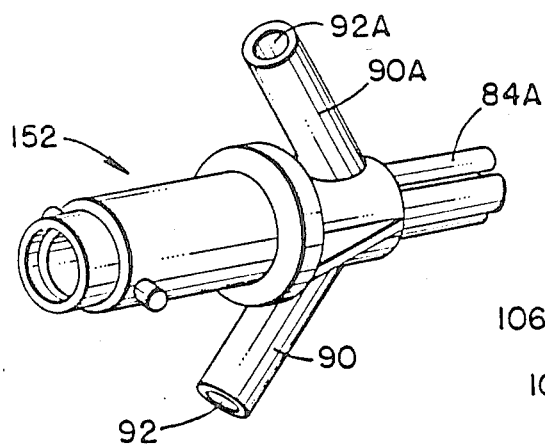
FIG. 11 is a perspective view of another embodiment of the connector.

With reference to FIG. 11, another embodiment of the invention is disclosed. Specifically, a connector 152 is illustrated which has not only a lower duct member 90 as illustrated in FIG. 3, but an upper duct member 90A which has an internal passageway 92A which communicates with a passageway within an upper elongated member 84A, similar to the member 84. By reason of the FIG. 11 construction, the connector 152 can accommodate all three passageways in the tri-lumen tubing thereby substantially simplifying the manufacture and assembly of systems utilizing the trilumen tubing.

While preferred embodiments of the invention have been disclosed in detail, it should be understood by those skilled in the art that various modifications may be made to those embodiments disclosed without departing from the scope thereof as described in the specification and defined in the appended claims.

What is claimed is:

1. A quick disconnect connector for use in a system for measuring depth of anesthesia of a patient, the system including a cylindrical female receptacle having a base and a terminal circular edge and a sidewall extending between the base and the edge to thereby define a receiving cavity having a longitudinal axis, the female receptacle having a pair of diametrically opposed bayonet slots formed therein, each slot extending generally parallel to the longitudinal axis for a first distance then curving to extend generally perpendicular to the longitudinal axis for a second distance, the slots extending in the same direction, each to its own terminus; and a resilient gasket received in the cavity adjacent the base; said connector adapted to be joined to multi-lumen tubing having at least a central conduit and a lower conduit, comprising:

a main body having a chamber therein, a longitudinal axis, and a first end terminating at a rim defining an opening into the chamber and having a second end opposite said first end;

a first elongated member integral with said main body and extending away from said second end and having a passageway extending therethrough communicating with the chamber, said first member being generally aligned with the longitudinal axis of said main body and fittingly receivable within the central conduit of the associated multi-lumen tubing;

said first end being a cylindrical male element having radially directed bayonet pins extending in diametrically opposed directions engageable with the mating bayonet slots in the female receptacle such that, with said first end aligned with the cavity in the female receptacle, said first end is inserted therein toward the base and turned about the longitudinal axis as it proceeds until each of said pins reaches its associated terminus, said rim being engaged with said gasket to thereby achieve a fluid tight junction between said connector and said female receptacle;

a duct member integral with said main body extending transversely therefrom and having a passage extending therethrough; and a second elongated member integral with said main body and extending away from said second end and having a passageway extending therethrough communicating with the passageway in said duct member, said second elongated member being fittingly receivable in the lower conduit.

2. A connector as set forth in claim 1 including:
   a plug member integral with said main body and extending away from said second end, said plug member being fittingly receivable in the upper conduit to prevent flow of the liquid beyond said connector.

3. A connector as set forth in claim 1 wherein said first elongated member includes a pair of enlarged sections in side by side relationship joined by a central web member, said enlarged sections and said central web member extending for the length thereof, each of the enlarged sections having a passageway therethrough communicating with the chamber.

4. A connector as set forth in claim 3 wherein the multi-lumen tubing is tri-lumen tubing having an upper conduit; and including:

a plug member integral with said main body and extending away from said second end, said plug member extending proximate and substantially parallel to said central web member and being fittingly receivable in the upper conduit to thereby seal the upper conduit at said connector.

5. A connector as set forth in claim 1 wherein said connector is adapted to be joined to the tri-lumen tubing having an upper conduit in addition to the central conduit and the lower conduit; said main body having a longitudinal axis, an upper side, and a lower side; said first elongated member being generally aligned with the longitudinal axis of said main body and being fittingly receivable in the central conduit; and including:
- a first duct member integral with said main body extending transversely from said upper side and having a passageway extending therethrough;
- a second duct member integral with said main body extending transversely from said lower side and having a passageway extending therethrough;
- an upper elongated member integral with said main body and extending away from said second end and having a passageway extending therethrough communicating with the passageway in said upper duct member, said upper elongated member being fitingly received in the upper conduit; and
- a lower elongated member integral with said main body and extending away from said second end and having a passageway extending therethrough communicating with the passageway in said lower duct member, said lower elongated member being fittingly receivable in the lower conduit.

6. A connector as set forth in claim 5 wherein said main body has a longitudinal axis, said first elongated member being generally aligned with the longitudinal axis of said main body; and wherein said first elongated member includes a pair of enlarged sections in side by side relationship joined by a central web member, said enlarged sections and said central web member extending for the length thereof, each of the enlarged sections having a passageway therethrough communicating with the chamber.

7. A connector as set forth in claim 6 wherein: said first elongated member has upper and lower surfaces, said upper elongated member being proximate and substantially parallel to said upper surface, said lower elongated member being proximate and substantially parallel to said lower surface.

8. A quick disconnect connector for joining multi-lumen tubing having at least first and second conduits therein to a cylindrical female receptacle of the bayonet connection type comprising:
- a main body having a longitudinal axis and a chamber therein and a first end terminating at a rim defining an opening into the chamber and having a second end opposite said first end;
- a first elongated member integral with said main body and extending away from said second end and having a passageway extending therethrough communicating with the chamber, said first member being generally aligned with the longitudinal axis of said main body and fittingly receivable in the first conduit and including a pair of enlarged sections in side by side relationship joined by a central web member, said enlarged sections and said central web member extending for the length thereof, each of said enlarged sections having a passageway therethrough communicating with the chamber;
- said first end being a cylindrical male element having radially directed bayonet pins extending in diametrically opposed directions engageable with mating bayonet slots in the female receptacle such that, with said first end being aligned with a cavity in the female receptacle, said first end is inserted therein toward a gasket positioned at a base of the cavity and turned about the longitudinal axis as it proceeds until each of said pins reaches its associated terminus, said rim being engaged with said gasket to thereby achieve a fluid tight junction between said connector and said female receptacle;
- a duct member integral with said main body extending transversely therefrom and having a passageway extending therethrough; and
- a second elongated member integral with said main body and extending away from said second end and having a passageway extending therethrough communicating with the passageway in said duct member; said second elongated member being fittingly receivable in the second conduit.

9. A connector as set forth in claim 8 wherein the multi-lumen tubing has first, second, and third conduits extending therethrough; and wherein
said first elongated member is generally aligned with the longitudinal axis of said main body and is fittingly receivable in the first conduit; and including:
- a duct member integral with said main body extending transversely therefrom and having a passageway extending therethrough;
- a second elongated member integral with said main body and extending away from said second end and having a passageway extending therethrough communicating with the passageway in said duct member, said second elongated member being fittingly receivable in the second conduit; and
- a plug member integral with said main body and extending away from said second end, said plug member being fittingly receivable in the third conduit to thereby terminate the third conduit at said connector.

10. A connector as set forth in claim 8 wherein: said main body has a longitudinal axis, an upper side, and a lower side, said first elongated member being generally aligned with the longitudinal axis of said main body and being fittingly receivable in the first conduit; and including:
- a first duct member integral with said main body extending transversely from said upper side and having a passageway extending therethrough;
- a second duct member integral with said main body extending transversely from said lower side and having a passageway extending therethrough;
- an upper elongated member integral with said main body and extending away from said second end and having a passageway extending therethrough communicating with the passageway in said upper duct member, said upper elongated member being fittingly receivable in the second conduit; and a lower elongated member integral with said main body and extending away from said second end and having a passageway extending therethrough communicating with the passageway in said lower duct member, said lower elongated member being fittingly receivable in the third conduit.

11. A quick disconnect connector for joining multi-lumen tubing having first, second, and third conduits extending therethrough to a cylindrical female receptacle of the bayonet connection type comprising:

a main body having a longitudinal axis and a chamber therein and a first end terminating at a rim defining an opening into the chamber and having a second end opposite said first end; and a first elongated member integral with said main body, generally aligned with the longitudinal axis thereof, and extending away from said second end and having a passageway extending therethrough communicating with the chamber, said first member being fittingly receivable in the first conduit;

said first end being a cylindrical male element having radially directed bayonet pins extending in diametrically opposed directions engageable with mating bayonet slots in the female receptacle such that, with said first end being aligned with a cavity in the female receptacle, said first end is inserted therein toward a gasket positioned at a base of the cavity and turned about the longitudinal axis as it proceeds until each of said pins reaches its associated terminus, said rim being engaged with said gasket to there by achieve a fluid tight junction between said connector and said female receptacle;

a duct member integral with said main body extending transversely therefrom and having a passageway extending therethrough;

a second elongated member integral with said main body and extending away from said second end and having a passageway extending therethrough communicating with the passageway in said duct member, said second elongated member being fittingly receivable in the second conduit; and a plug member integral with said main body and extending away from said second end, said plug member being fittingly receivable in the third conduit to thereby terminate the third conduit at said connector.

* * * * *